United States Patent [19]

Marlettini et al.

[11] Patent Number: 4,522,827
[45] Date of Patent: Jun. 11, 1985

[54] METHOD OF TREATING ACUTE PANCREATITIS WITH ISOMETHEPTENE

[75] Inventors: Maria G. Marlettini; Michelangelo DeNovellis; Ernesto Labriola; Teresa Salomone; Paola Tomassetti, all of Bologna, Italy

[73] Assignee: Knoll AG, Fed. Rep. of Germany

[21] Appl. No.: 394,797

[22] Filed: Jul. 2, 1982

[51] Int. Cl.³ .............................................. A61K 31/13
[52] U.S. Cl. ..................................... 514/671; 514/960
[58] Field of Search .......................................... 424/325

[56] References Cited

PUBLICATIONS

Merck Index, 9th Ed., 1976, No. 5040; 5815.
H. Conn, Current Therapy, pp. 486–489, Acute Pancreatitis, 1981.
Gilman et al, The Pharmacological Basis of Therapeutics, 6th Ed., 1980, p. 133.

*Primary Examiner*—Albert T. Meyers
*Assistant Examiner*—John W. Rollins
*Attorney, Agent, or Firm*—Keil & Weinkauf

[57] ABSTRACT

A method of relieving the symptoms of acute pancreatitis comprising administering Isometheptene to a person afflicted with that condition.

3 Claims, 4 Drawing Figures

4,522,827

METHOD OF TREATING ACUTE PANCREATITIS WITH ISOMETHEPTENE

BACKGROUND OF THE INVENTION

This invention relates to a method for relieving symptoms of acute pancreatitis in mammals. More particularly, the invention concerns a method for treating persons afflicted with acute pancreatitis by administering to such a person a sufficient amount of Isometheptene to effectively relieve symptoms of that disease.

Acute pancreatitis causes pathologic changes in the pancreas ranging from a mild edematous process to an overwhelming necrotizing lesion which may be life-threatening. While its symptoms are variable it is principally characterized by epigastric pain radiating to either the upper quadrant or directly through to the back. The typical pain is gnawing, of sudden onset, of exceeding severity, unremitting, and sometimes colicky in character. It is not relieved by vomiting and is little affected by morphine, for example. Patients with this condition are also commonly found to have persistent high amylase in the blood and urine and frequently develop shock due to circulating vasoactive substances or retroperitoneal hemorrhage.

A standard rationale in treating this condition is to set the gland to rest, such as by restricting the intake of food, administering fluids, and maintaining electrolyte balance. Treatment involving the use of various drug compositions has also been attempted previously, including the use of specific drugs which are known to inhibit gastric and/or pancreatic secretions such as Aprotinin, but none of these treatments appears to exhibit any proven overall benefit.

SUMMARY OF THE INVENTION

Accordingly, it is an object of this invention to provide a treatment for acute pancreatitis which is effective in relieving its symptoms and in managing the patient's condition until a state of relative normalcy is obtained. This and other objects of the invention are attained by administering to a patient afflicted with acute pancreatitis an effective amount of Isometheptene to alleviate symptoms of that disease, especially by relieving the attendant pain and inhibiting pancreatic secretions. In one embodiment of the invention, the intended result is accomplished by an initial infusion of Isometheptene at a dosage level of 0.9–2.5 grams per twenty-four (24) hours until the symptoms are substantially diminished, followed by an oral maintenance dosage of 0.15 grams every six (6) hours for about ten (10) to fifteen (15) days.

BRIEF DESCRIPTION OF THE DRAWINGS

In the drawings, which are set forth to illustrate the results of clinical testing described in the example, the figures are as follows.

DETAILED DESCRIPTION OF THE INVENTION

Figure 1:
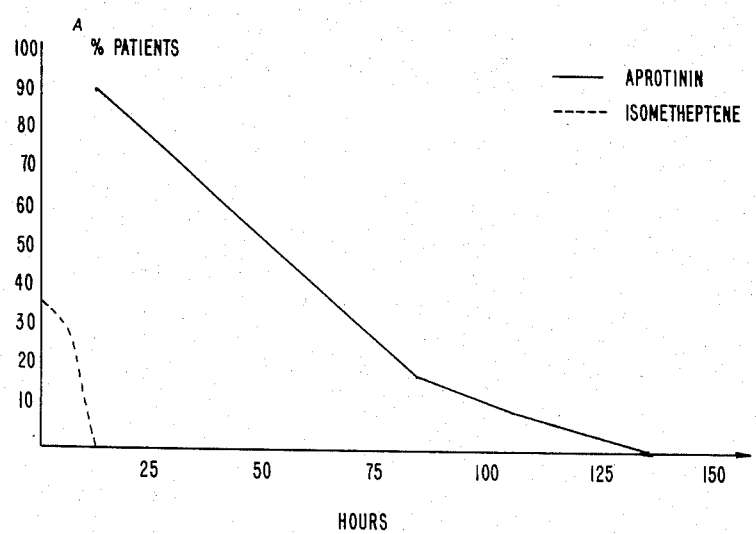
FIG. 1 is a graph illustrating the time-response relationship of Aprotinin and Isometheptene, respectively, on pain, expressed as the percentage of test patients experiencing pain over a period of hours.

In accordance with the practice of this invention, a novel treatment for acute pancreatitis is provided by administering to a person suffering from that condition an effective amount of Isometheptene to relieve its symptoms, especially the attendant pain, and inhibit the enzymatic secretions of the pancreas.

Isometheptene (N,1,5-Trimethyl-4-hexenylamine) is a sympathomimetic aliphatic amine with a mainly beta-mediated action. It is a well-known, commercially available drug; for example, it is available under the trademark OCTIN from Knoll A. G. of West Germany. It was first prepared according to the process described in U.S. Pat. No. 2,230,753 (1941), and in its hydrochloride or mucate salt form it is soluble in water. As used herein, the term Isometheptene should be read to include its pharmacologically acceptable acid addition salts.

According to the invention, the compositions useful in this invention may be administered either parenterally or orally, although it is preferred that in the initial stages of treatment, Isometheptene is administered by infusion until the attendant pain and high amylase serum levels are dimished. The patient can then be placed on a maintenance schedule using compositions adapted for oral administration such as tablets, pills, or capsules.

The formulation of the compositions utilized in this invention, whether in the form of tablets or pills, or in an injectable form, may be carried out in the manner normally employed in the art. When adapted for enteral use, this usually includes combining the active ingredient, i.e. Isometheptene, with pharmaceutically acceptable inorganic or organic excipients which are suitable for such administration. These include carriers, binders, fillers, lubricants, stabilizers, preservants, wetting agents, and the like. The quantities of these substances may vary widely and depend upon the physical characteristics and size of the orally applicable composition, the method of its manufacture, and the like. If desired, the compositions used in this invention may contain other therapeutically useful substances. The concentration of Isometheptene utilized in either the injectable or enteral form may be varied to provide for the desirable dosage. It is normally preferable to have Isometheptene present in an injectable solution in a concentration of about 1 gram or less (preferably about 0.5 grams—0.25 grams or less) per each 10 milliliter of the injectable solution. The intended results of this invention are preferably accomplished by an initial infusion of Isometheptene at a dosage level of 0.9–2.5 grams per twenty-four (24) hours until the symptoms are substantially diminished, followed by an oral maintenance dosage of 0.15 grams every six (6) hours for about ten (10) to fifteen (15) days.

The following example illustrates the unique effectiveness of Isometheptene in treating acute pancreatitis. However, it is in no way intended to limit the present invention. Unless otherwise indicated, all parts, wherever given in the specification, are parts by weight.

EXAMPLE

Patients afflicted with acute pancreatitis were divided into two groups and treated, respectively, with Isometheptene and with a standard drug, Aprotinin. In selecting the patients for this trial, the following criteria was established:

Each of the patients exhibited a clinical picture of acute pancreatitis lasting not longer than eight hours before admittance to the study, and serum amylase activity of more than three times the upper limit of normal and/or a urinary amylase concentration over twice the upper limit of normal. When diagnosed, the severity of the disease was rated as mild (abdominal pain and tension), moderate (tension with guarding and paralytic ileus), or severe (paralytic ileus with diffused peritonitis and/or shock). Patients with hypertension and mild coronary artery disease were also included in the trial. Previous cardiovascular therapy in those cases was maintained. They were randomly allocated to two groups designated Group A and Group B and received the standardized basic treatment, that is strict bed rest, restriction from oral fluid and food, antacids (Maalox, Rohrer 15 milliliters per four (4) hours) for at least four days, antibiotics (cephazolin 2 g i.m./24 hrs.) and 2.5–3 l i.v. fluid (according to the central venous pressure) for six (6) days, electrolyte substitution (K, Ca) being added if needed.

The composition and etiology for each group is shown below:

TABLE I

| | Group A (Aprotinin) No. of Patients | Group B (Isometheptene) No. of patients |
|---|---|---|
| men | 10 | 13 |
| women | 8 | 6 |
| total | 18 | 19 |
| Age (yr) (mean and range) | 52 (33–70) | 55 (21–72) |
| Severity of disease at the time of admission | | |
| mild | 7 | 7 |
| moderate | 11 | 12 |
| severe | — | — |
| Etiology | | |
| acute relapsing pancreatitis (at least one former attack) with severe alcoholism | — | 2 |
| acute pancreatitis with severe alcoholism | 3 | 5 |
| acute pancreatitis with disease of biliary tract | 12 | 12 |
| acute pancreatitis with disease of biliary tract and severe alcoholism | 1 | — |
| acute pancreatitis without alcoholism or known disease of biliary tract | 2 | — |

Each of the patients selected for Group A was given Aprotinin 1.500.000 U/24 hours and analgesics (aminophenazone and pentazozine) when needed. When symptoms of the disease had improved, the dosage was accordingly diminished. The treatment was maintained until amylase activity had become normal except for three patients without normalization of serum and urinalysis after a month. Afterwards, analgesic drugs were given if needed.

The individuals selected for Group B were each given Isometheptene as a continuous infusion for twenty-four (24) hours (0.9–2/5 grams/24 hrs.) according to the severity of the disease. As the symptoms improved, the dosage was diminished. Afterwards, oral treatment with Isometheptene 0.15 grams/6 hrs. was initiated and maintained for fifteen (15) days. The administration of analgesics to this group was forbidden.

The protocol of the follow-up study was in accordance with Goebell et al (Scand. J. Gastroent. 1979, 14, 881–889) in which the duration of adominal pain was particularly assessed along with the duration of abnormal amylase activity both in the serum and urine. In addition, when the treatment was started, the mean fall of serum amylase after 0.3 g i.v. of Isometheptene in Group B was evaluated. The same was considered after 500.000 U i.v. of Aprotinin in three patients of Group A. At the end of the treatment the severity of the disease course was graded according to the criteria defined by Trapnell et al (Brit. J. Surg. 1974, 61, 177–182) and compared with the severity of the disease at the beginning.

Figure 2:
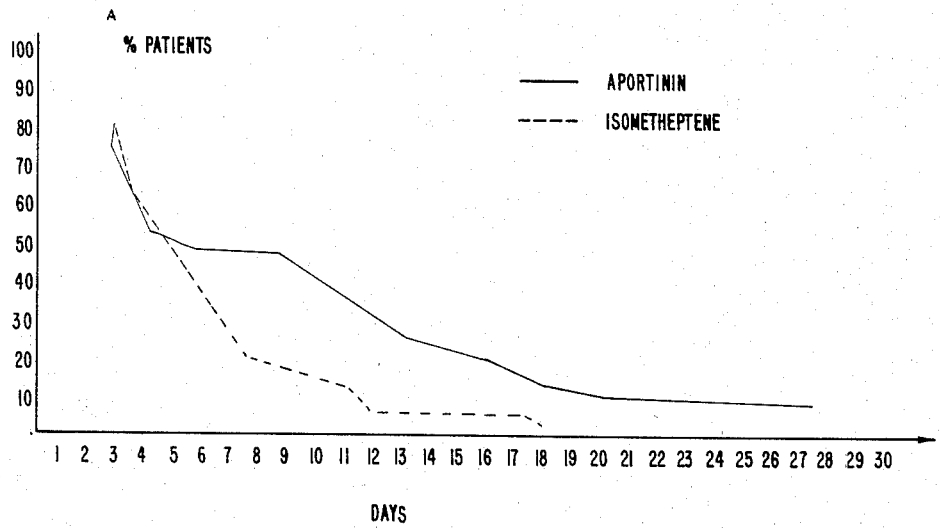
FIG. 2 is a graph showing the time-response relationship of Aprotinin and Isometheptene, respectively, on patients with abnormal serum and urine amylase on a day by day basis.
Figure 3:
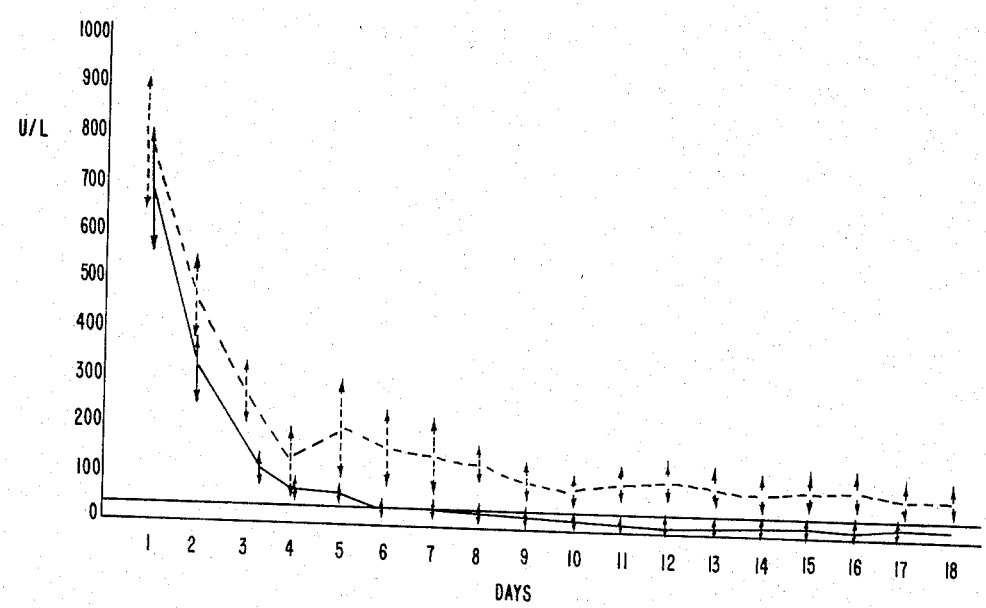
FIG. 3 is a graph depicting the mean fall of serum amylase activity over the course of the treatment with either Aprotinin or Isometheptene on a day-by-day basis (Mean±SEM).

With regard to Group A, as illustrated in FIG. 1, abdominal pain lasted $74.4 \pm 10.4$ hours. Abnormal amylase activity in serum and urine lasted $10.2 \pm 8.1$ days (see FIGS. 2, 3). This includes 3 patients whose serum and urine amylase activity was still abnormal after a month when they underwent surgery: two of them for gallbladder stones, the other one for slerosis of the choledocho-duodenal sphincter. Mild and unsteady increase in urine amylase remained in patients with alcoholic pancreatitis.

According to the Trapnell criteria, the course of the disease remained mild in seven patients and moderate in eleven.

Two patients had pleural effusion on the left side, while in one patient without previous diabetes blood glucose rose significantly. Two patients in Group A relapsed in the course of the disease.

In Group B, again as shown in FIG. 1, abdominal pain lasted $4.4 \pm 0.59$ hours. The difference from Group A is statistically highly significant ($p < 0.01$). The abnormal amylase activity in serum and urine lasted $3.8 \pm 2.5$ days (see FIGS. 2, 3). The difference from Group A is also statistically significant ($p < 0.05$). (Standard statistical methods were utilized in this regard including the random text; the Wilcoxon, Mann, Whitney test; the Kolmogorov-Smirnov test; the median test; the t test for unpaired data; and the survivor tables. The mean and standard deviation are given in the statistical values.)

Figure 4:
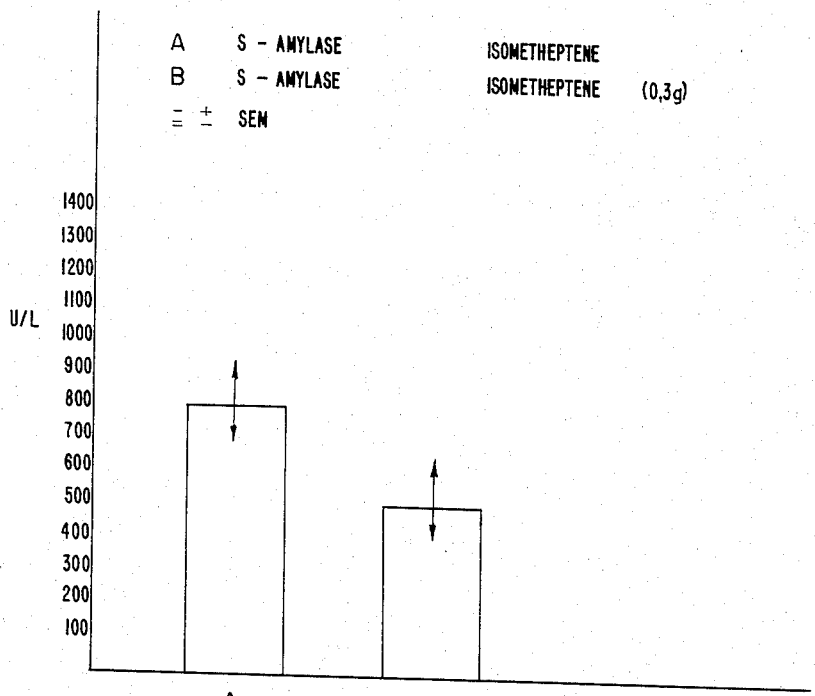
FIG. 4 is a graph illustrating the mean fall of serum amylase after the administrating of Isometheptene 0.3 gi.v. (Mean±SEM).

The course of acute pancreatitis which started as moderate in Groups A and B was also compared. The duration of the disease was $17.1 \pm 6.7$ days in Group A, and $5.7 \pm 3.2$ days in Group B; the difference was significant ($p < 0.01$). The mean fall in serum amylase after 0.3 g of Isometheptene as an intravenous infusion was $291.3 \pm 207.26$ (see FIG. 4). However, there was no significant fall in serum amylase activity after the administration of Aprotinin 500.000 U.

In Group B, The course of the disease, which began as moderate in twelve patients, was mild in eleven patients, and remained moderate in one patient. A mild and unsteady increase in urine amylase remained in patients with alcoholic pancreatitis. No adverse reactions were observed in the group. There were no relapses in Group B patients.

These data illustrate the significant effect of Isometheptene on pain and on the duration of abnormal amylase activity in serum and urine, especially in those cases which had started in a moderate form. Furthermore, while there were no relapses in the group of patients treated with Isometheptene, relapses did occur in those treated with Aprotinin. Little or no increase in heart rate and blood pressure, and no worsening of the coronary artery disease was found to exist where Isometheptene was administered.

It should be understood that this invention may be embodied in other specific forms without departing from its spirit or essential characteristics. Accordingly, the present embodiments are to be considered in all respects as illustrative and not restrictive, the scope of the invention being indicated by the appended claims rather than by the foregoing description, and all changes which come within the meaning and range of equivalency of the claims are intended to be embraced therein.

The following compositions can be used according to the invention:

Composition 1

Tablets of the following composition are obtained in a conventional manner, using a tablet press:
100 mg of isometheptene,
240 mg of corn starch,
27 mg of gelatine,
90 mg of lactose,
45 mg of talc,
4.5 mg of Aerosil ® (chemically pure, finely divided silica containing submicroscopic particles), and
13.5 mg of potato starch (as a 6% strength paste)

Composition 2

Coated tablets of the following composition are prepared in a conventional manner;
60 mg of isometheptene,
120 mg of core material, and
120 mg of sugar-coating mixture.

The core material consists of 9 parts of corn starch, 3 parts of lactose and 1 part of Luviskol ®VA 64 (60:40 vinylpyrrolidone/vinyl acetate copolymer, cf. Pharm. Ind. 1962, 586). The sugar-coating mixture consists of 5 parts of sucrose, 2 parts of corn starch, 2 parts of calcium carbonate and 1 part of talc. The coated tablets thus prepared are then provided with a final coating which is resistant to gastric juices.

Composition 3

10 g of isometheptene hydrochloride are dissolved in 5,000 ml of water. The pH of the solution is adjusted to 7.2 and NaCl is added until a bloodisotonic solution results. 1 l of the solution is introduced into infusion bags and the bags are sterilized.

Composition 4

100 g of isometheptene hydrochloride are dissolved in 1 l of water, with the addition of 1 g $Na_2HPO_4.12H_2O$. 1 ml of the solution is introduced into each ampoule and the ampoules are sterilized.

We claim:

1. A method for treating acute pancreatitis which comprises administering by infusion to a person afflicted with that condition an effective amount of Isometheptene contained in an injectable solution to relieve the attendant pancreatitis symptoms followed by orally administered dosages of a composition containing an effective amount of Isometheptene and a pharmaceutically acceptable excipient.

2. A method according to claim 1 wherein Isometheptene is initially administered by infusion at a dosage level of 0.9-2.5 g per twenty-four (24) hours until the symptoms diminish, followed by an orally administered dosage of 0.15 g about every six (6) hours for about ten (10)-fifteen (15) days.

3. A method of relieving pain and inhibiting pancreatic secretions associated with acute pancreatitis in a person afflicted with that condition which comprises initially administering by infusion to said afflicted person an injectable solution of Isometheptene containing up to 1 gram of Isometheptene per each 10 milli-liters of the solution at a dosage level of 0.9-2.5 g per twenty-four (24) hours until the pain diminishes followed by an orally administered dosage of 0.15 g of Isometheptene about every six (6) hours for about ten (10)-fifteen (15) days.

* * * * *